(12) United States Patent
Li et al.

(10) Patent No.: US 9,204,844 B2
(45) Date of Patent: *Dec. 8, 2015

(54) SYSTEM AND METHOD FOR REMOVING ARTIFACTS FROM WAVEFORMS

(71) Applicant: COVIDIEN LP, Mansfield, MA (US)

(72) Inventors: Li Li, Petaluma, CA (US); Paul D. Mannheimer, Danville, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,321

(22) Filed: Apr. 17, 2014

(65) Prior Publication Data

US 2014/0228658 A1  Aug. 14, 2014

Related U.S. Application Data

(63) Continuation of application No. 12/785,295, filed on May 21, 2010, now Pat. No. 8,744,543, which is a continuation of application No. 11/241,509, filed on Sep. 29, 2005, now Pat. No. 7,725,147.

(51) Int. Cl.
| | |
|---|---|
| *A61B 5/1455* | (2006.01) |
| *A61B 5/02* | (2006.01) |
| *A61B 5/00* | (2006.01) |
| *G06K 9/00* | (2006.01) |
| *A61B 5/024* | (2006.01) |

(52) U.S. Cl.
CPC ........... *A61B 5/7207* (2013.01); *A61B 5/02416* (2013.01); *A61B 5/14551* (2013.01); *A61B 5/4875* (2013.01); *G06K 9/00516* (2013.01)

(58) Field of Classification Search
CPC .......... A61B 5/02416; A61B 5/14551; A61B 5/4875; A61B 5/7207
See application file for complete search history.

(56) References Cited

U.S. PATENT DOCUMENTS

| | | |
|---|---|---|
| 4,802,486 A | 2/1989 | Goodman et al. |
| 4,807,630 A | 2/1989 | Malinouskas |

(Continued)

FOREIGN PATENT DOCUMENTS

| | | |
|---|---|---|
| WO | 9516387 | 6/1995 |
| WO | 9843071 | 10/1998 |
| WO | 03000125 | 1/2003 |
| WO | 2004075746 | 9/2004 |

OTHER PUBLICATIONS

Ikeda, Kenji, et al.; "Improvement of Photo-Electric Plethysmograph Applying Newly Developed Opto-Electronic Devices;" IEEE Tencon, pp. 1109-1112 (1999).

(Continued)

*Primary Examiner* — Eric Winakur
(74) *Attorney, Agent, or Firm* — Fletcher Yoder PC

(57) ABSTRACT

A technique is provided for processing a physiological signal to compensate for artifacts. The technique includes identifying artifacts within the physiological signal. The technique also includes performing one or more multi-resolution decompositions, such as wavelet transformations, on the physiological signal and compensating for the identified artifacts in some or all of the respective decomposition components. The modified decomposition components may be reconstructed to generate an artifact-compensated signal which may be provided to a monitor or other device which is otherwise not configured to compensate for signal artifacts.

21 Claims, 4 Drawing Sheets

(56) References Cited

U.S. PATENT DOCUMENTS

| | | | |
|---|---|---|---|
| 4,911,167 | A | 3/1990 | Corenman et al. |
| 4,928,692 | A | 5/1990 | Goodman et al. |
| 4,934,372 | A | 6/1990 | Corenman et al. |
| 4,972,331 | A | 11/1990 | Chance |
| 5,122,974 | A | 6/1992 | Chance |
| RE35,122 | E | 12/1995 | Corenman et al. |
| 6,361,501 | B1 | 3/2002 | Amano et al. |
| 6,393,311 | B1 | 5/2002 | Edgar, Jr. et al. |
| 6,519,486 | B1 | 2/2003 | Edgar, Jr. et al. |
| 6,584,336 | B1 | 6/2003 | Ali et al. |
| 6,650,918 | B2 | 11/2003 | Terry |
| 6,654,623 | B1 | 11/2003 | Kastle |
| 6,658,277 | B2 | 12/2003 | Wasserman |
| 6,850,787 | B2 | 2/2005 | Weber et al. |
| 6,931,269 | B2 | 8/2005 | Terry |
| 7,025,724 | B2 | 4/2006 | Adam et al. |
| 7,027,850 | B2 | 4/2006 | Wasserman |
| 7,060,035 | B2 | 6/2006 | Wasserman |
| 7,099,714 | B2 | 8/2006 | Houben |
| 7,139,599 | B2 | 11/2006 | Terry |
| 7,215,984 | B2 | 5/2007 | Diab |
| 7,373,194 | B2 | 5/2008 | Weber et al. |
| 7,515,949 | B2 | 4/2009 | Norris |
| 8,073,516 | B2 | 12/2011 | Scharf |
| 2004/0039273 | A1 | 2/2004 | Terry |

OTHER PUBLICATIONS

Yang, Boo-Ho, et al.; "Development of the ring sensor for healthcare automation;" Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis;" Proceedings of the 22nd Annual EMBS International Conference, Chicago, Illinois; Jul. 23-28, 2000; pp. 2792-2795.

Aoyagi, T., et al.; "Pulse Oximeters: background, present and future;" Neonatal Care, vol. 13, No. 7, pp. 21-27 (2000) (Article in Japanese—contains English summary of article).

Rhee, Sokwoo, et al.; "Artifact-Resistant, Power-Efficient Design of Finger-Ring Plethysmographic Sensor;" IEEE Transactions on Biomedical Engineering, vol. 48, No. 7, pp. 795-805 (Jul. 2001).

Lopez-Silva, Sonnia Maria Lopez, et al.; "NIR transmittance pulse oximetry system with laser diodes;" Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP);" Optomechanical Design and Engineering, Proceedings of SPIE, vol. 4444, pp. 285-293 (2001).

Prochazka, et al.; "Decomposition and Reconstruction Methods in Biomedical Image De-Noising;" Jun. 2002, Proc. 16th Beinnial Intl. Conference, pp. 350-352.

Tobata, H., et al.; "Study of Ambient Light Affecting Pulse Oximeter Probes;" Ikigaku (Medical Technology), vol. 71, No. 10, pp. 475-476 (2002) (Article in Japanese—contains English summary of article).

Shaltis, Phillip, et al.; "Implementation and Validation of a Power-Efficient, High-Speed Modulation Design for Wireless Oxygen Saturation Measurement Systems;" IEEE, pp. 193-194 (2002).

Itoh, K., et al.; "Pulse Oximeter" Toyaku Zasshi (Toyaku Journal), vol. 25, No. 8, pp. 50-54 (2003) (Article in Japanese—contains English summary of article).

Johnston, William S., et al.; "Effects of Motion Artifacts on helmet-Mounted Pulse Oximeter Sensors;" 2 pgs. (2004).

SYSTEM AND METHOD FOR REMOVING ARTIFACTS FROM WAVEFORMS

CROSS-REFERENCE TO RELATED APPLICATIONS

This application is a continuation of U.S. application Ser. No. 12/785,295, titled "System and Method for Removing Artifacts from Waveforms," filed May 21, 2010, which is a continuation of U.S. application Ser. No. 11/241,509, titled "System and Method for Removing Artifacts from Waveforms," filed Sep. 29, 2005, now U.S. Pat. No. 7,725,147, the disclosures of which are each hereby incorporated by reference in their entirety for all purposes.

BACKGROUND OF THE INVENTION

1. Field of the Invention

The present invention relates generally to the processing of waveform data and, more particularly, to the processing of waveforms associated with medical monitoring.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

The quality of these measurements, however, may be adversely affected by a number of factors such as patient motion, subdermal physiological structures, poor sensor operation or fit, poor signal reception and transmission, and so forth. Such factors may result in a pulse oximetry signal which contains artifacts or noise or is otherwise of low or reduced quality. When processed, such a low or reduced quality signal may result in physiological measurements being reported which may not be as accurate or reliable as desired.

To address this issue of poor signal quality, newer pulse oximetry monitors and/or systems may include algorithms, circuits, or other components to reduce, remove, or otherwise compensate for artifacts within the pulse oximetry signal. Such artifact compensation techniques, however, may be unavailable to health care providers using older or less advanced equipment that is not configured for artifact compensation. Since replacing older or less advanced pulse oximetry monitors and/or systems may not be financially feasible, a health care provider may have little choice but to continue using a system or monitor that does not compensate for artifacts in the acquired signal. However, even if an artifact compensating system is available, an older or less advanced system may still be useful within a health care facility. It may, therefore, be useful to provide artifact compensation in conjunction with the use of systems otherwise not configured to compensate for noise and artifacts with the pulse oximetry signal.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a method for processing a physiological signal, the method including the acts of: identifying one or more artifacts in a physiological signal; performing one or more multi-resolution decompositions on the physiological signal to generate two or more decomposition products; and compensating for the one or more artifacts in the two or more decomposition products to generate modified decomposition products.

There is provided one or more machine-readable media, including: a routine configured to identify one or more artifacts in a physiological signal; a routine configured to perform one or more multi-resolution decompositions on the physiological signal to generate two or more decomposition products; and a routine configured to compensate for the one or more artifacts in the two or more decomposition products to generate modified decomposition products.

There is provided a physiological monitoring system, including: a sensor configured to generate a physiological signal; and a monitor configured to receive an artifact-compensated signal derived from the physiological signal, wherein the artifact-compensated signal is generated by identifying one or more artifacts in the physiological signal, by performing one or more multi-resolution decompositions on the physiological signal to generate two or more decomposition products; by compensating for the one or more artifacts in the two or more decomposition products to generate modified decomposition products, and by reconstructing the modified decomposition products to generate the artifact-compensated signal.

There is provided a physiological sensor, including: an emitter configured to emit light; a detector configured to generate a signal in response to the emitted light; and one or more processing components configured to process the signal to generate an artifact-compensated signal.

There is provided a cable, including: one or more processing components configured to process an initial signal to generate an artifact-compensated signal.

There is provided an electronic device, including: one or more processing components configured to receive a signal generated by a physiological sensor, to process the signal to generate an artifact-compensated signal, and to transmit the artifact-compensated signal to a monitor which is not configured to perform artifact compensation

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a pulse oximeter signal (or other physiological monitor signal) from which the artifacts (such as may be generated by patient motion, subdermal physiological structures, poor sensor operation or fit, poor signal reception and transmission, and so forth) have been removed or reduced. Such a "clean" output signal may be provided as an input to a monitor or other display device which is not itself configured to compensate for signal noise or artifacts. The monitor or display device may display the clean signal or process the clean signal to generate one or more physiological characteristics of interest, such as measurements of blood oxygen level ($SpO_2$), pulse rate, and so forth. In accordance with some aspects of the present technique, the artifact and noise compensation may be performed by processing components located on the sensor itself, on a cable disposed between the sensor and the monitor or display device, or on an intermediate device, such as a conversion unit or intermediate monitor.

Figure 1:
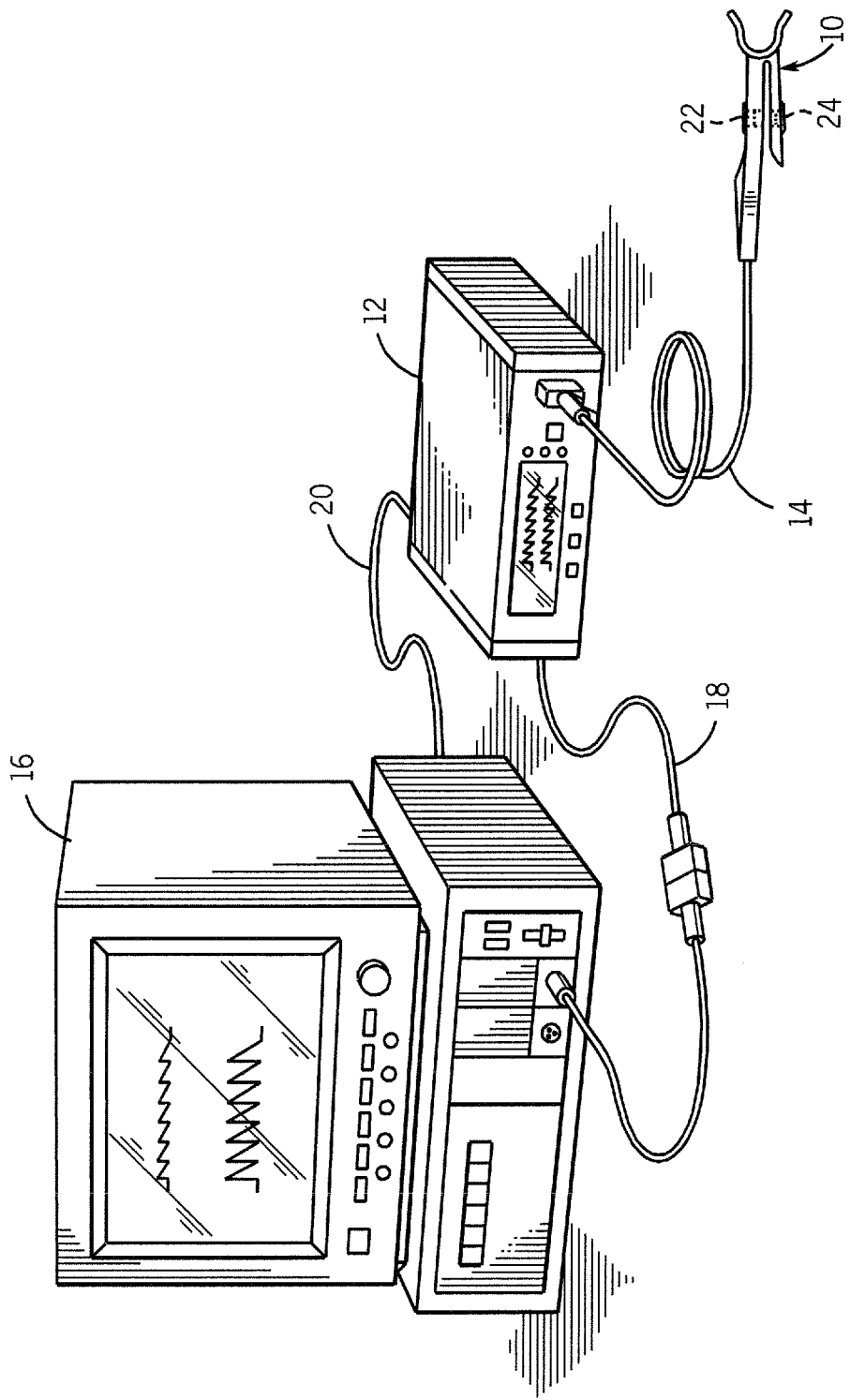
FIG. 1 illustrates a patient monitoring system coupled to a multi-parameter patient monitor and a sensor, in accordance with aspects of the present technique.

Turning now to FIG. 1, an exemplary medical monitoring system that may benefit from the present technique is depicted. The exemplary system includes a physiological sensor 10 that may be attached to a patient. The sensor 10 generates an output signal based on a monitored physiological characteristic and transmits the output signal to a patient monitor 12. In the depicted embodiment, the sensor 10 is connected to the patient monitor 12 via a cable 14 suitable for transmission of the output signal as well as any other electrical and/or optical signals or impulses communicated between the sensor 10 and monitor 12. In accordance with aspects of the present technique, the sensor 10 and/or the cable 14 may include or incorporate one or more integrated circuit devices or electrical devices, such as a memory, processor chip, or resistor that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors. In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12.

In one embodiment, the patient monitor 12 may be a suitable pulse oximeter, such as those available from Nellcor Puritan Bennett Inc. In other embodiments, the patient monitor 12 may be a monitor suitable for measuring other physiological characteristics (such as tissue water fraction, tissue or blood carbon dioxide levels, and so forth) using spectrophotometric or other techniques. Furthermore, the monitor 12 may be a multi-purpose monitor suitable for performing pulse oximetry and/or other physiological and/or biochemical monitoring processes using data acquired via the sensor 10. Furthermore, to provide additional or enhanced functions to those performed by the monitor 12, the patient monitor 12 may be coupled to a multi-parameter patient monitor 16 via a cable 18 connected to a sensor input port and/or via a cable 20 connected to a digital communication port.

As noted above the data provided to the monitor 12 (or, alternatively, to the multi-parameter monitor 16) is generated at the sensor 10. In the example depicted in FIG. 1, the sensor 10 is an exemplary spectrophotometry sensor (such as a pulse oximetry sensor or probe) that includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 through which electrical and/or optical signals may be transmitted to and/or from the emitter 22 and detector 24. The sensor 10 may be configured for use with the emitter and detector on the same side of the sensor site (i.e., as a "reflectance type" sensor) or on opposite sides of the sensor site (i.e., as a "transmission type" sensor). During operation, the emitter 22 shines one or more wavelengths of light through the patient's fingertip, or other tissue, and the light received by the detector 24 is processed to determine one or more physiological characteristics of the patient.

For example, for pulse oximetry applications the oxygen saturation of the patient's arterial blood ($SaO_2$) may be determined using two or more wavelengths of light emitted by the emitter 22, most commonly red and near infrared wavelengths. After passage through the patient's tissue, a portion of the light emitted at these wavelengths is detected by the detector 24. The detector generates one or more signals, such an electrical or optical signals, in response to the amount of each wavelength that is detected at a given time. The generated signals may be digital or, where acquired as analog signals, may be digitized in implementations where digital processing and manipulation of the signals is employed. Such digitalization may be performed at the monitor 12 or prior to reaching the monitor 12. The signals, as noted above, may be transmitted via the cable 14 to the monitor 12, where the oxygen saturation or other physiological characteristic is calculated based on the signals. The signals may contain artifacts due to a variety of factors, such as light modulation by subdermal anatomic structures, patient motion during data acquisition, poor sensor operation or fit, poor signal reception and transmission, and so forth.

In one implementation of the present technique, the monitor 12 is not configured to compensate for artifacts in the data signal (such as a pulse oximetry signal) provided by the sensor 10. In such an implementation, one or more of the upstream devices or structures (such as sensor 10 and/or cable 14) may be configured to process the data to compensate for artifacts and to, thereby, generate a clean signal for processing or display by the monitor 12. Similarly, in another implementation, a downstream monitor, such as multi-parameter monitor 16 or a further downstream monitor, is not configured to compensate for artifacts in the signal. In such an implementation, the upstream devices or structures that may process the signal to compensate for artifacts may include not only the sensor 10 and/or cable 14, but also the monitors 12 or 16 and/or additional intermediate cables 18, 20. Similarly, other intermediate devices or structures may be disposed between the sensor 10 and the target monitor to process the data signal to compensate for artifacts, thereby generating a clean signal.

Figure 2:
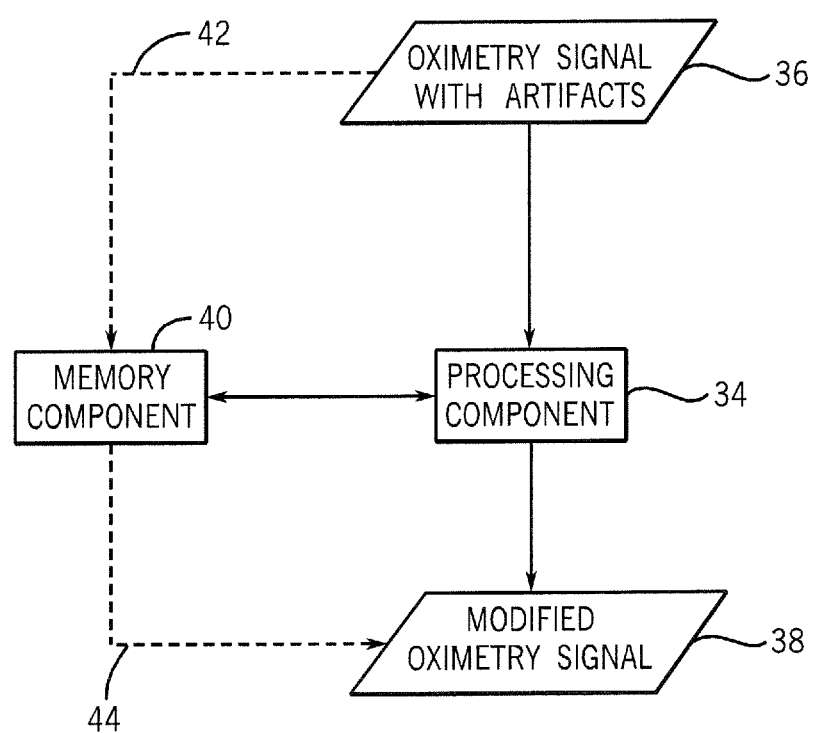
FIG. 2 is a diagram depicting components of a physiological signal processing system, in accordance with aspects of the present technique.

Referring now to FIG. 2, a box-diagram setting forth components used to process a signal to compensate for artifacts is set forth. In particular, a processing component 34 is depicted which is configured to receive an oximetry signal 36 containing artifacts and to compensate for the artifacts to produce a modified oximetry signal 38. The processing component 34 may be a general or special purpose processor or circuit suitable for incorporation into the desired structure, such as sensor 10 and/or cables 14, 18, or 20, as discussed above with regard to FIG. 1. Likewise, the processing component 34 may be a general or special purpose processor incorporated in the monitor 12, multi-parameter monitor 16, or other electronic device in the path along which the signal flows to a downstream destination that is not configured to compensate for signal artifacts.

While the processor component 34 may include hardware or circuitry designed to compensate for artifacts in the signal 36, the processor component 34 may also or alternately execute code or routines stored in a memory component 40 to accomplish the desired artifact compensation. The memory component 40 may be within the same device or structure as the processing component 34 or may be within a different structure or device in communication with the processing component 34. Such a memory components 40 may include solid state or integrated circuit type memory devices or other suitable memory devices, such as magnetic or optical media and/or drives suitable for use in the desired structure or device. As noted above, such processing components 34 and/or memory components 40 may be incorporated into the sensor 10, cables 14, 18, and 20, or the monitors 12, and 16.

FIG. 2 generally depicts that the signal 36 with artifacts is provided to the processing component 34 for artifact compensation. It is also possible, however, that the signal 36 is provided initially to the memory component 40 for subsequent processing by the processing component 34, as denoted by dotted line 42. Similarly, though the modified signal 38 may be directly output by the processing component 34 to a downstream location, it may also be stored temporarily by the memory component 40 prior to subsequent downstream transmission, as depicted by dotted line 44.

Figure 3:
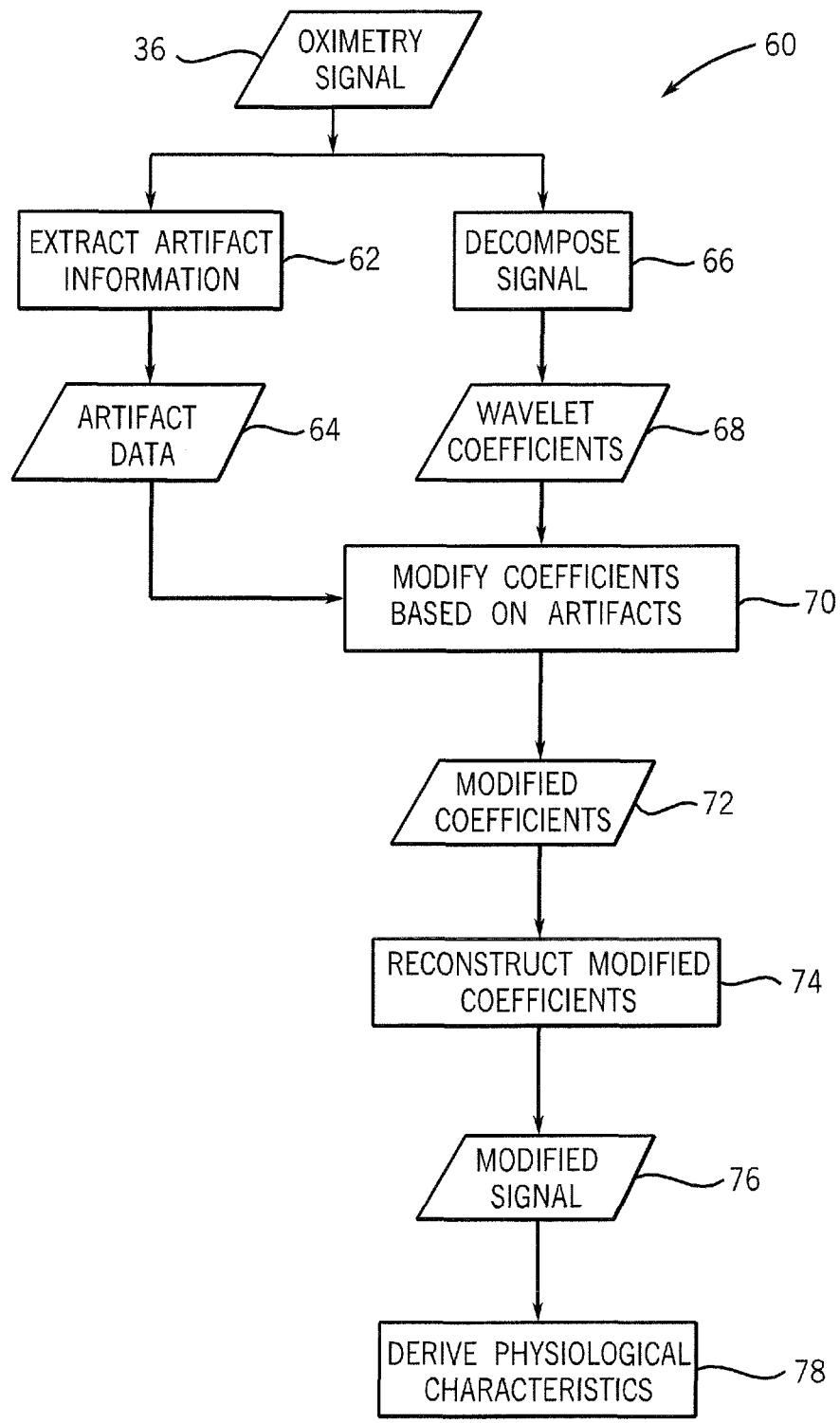
FIG. 3 is a flowchart of exemplary actions performed in accordance with aspects of the present technique.

In an embodiment of the present technique, a data signal containing artifacts is processed to compensate for those artifacts and may, subsequently, be provided to a monitor or other system that is otherwise not configured to compensate for artifacts in the signal. An example of such an embodiment is set forth in FIG. 3, depicting an artifact compensation technique 60 for use with a physiological signal. In this example, an oximetry data signal 36, such as a plethysmographic waveform, is processed to remove artifacts.

In this example, the oximetry signals 36 are processed to identify artifacts 64 within the signal (block 62). Identification of the artifacts 64 at block 62 may be accomplished by conventional artifact identification algorithms or techniques, such as may be implemented in advanced oximetry monitors or other processor-based systems commercially available or proprietary. In accordance with the present technique, these artifact identification techniques or algorithms may be implemented, as discussed above, by one or more processing components 34. These processing components 34 may be disposed within the sensor 10 itself, within the cables 14, 18, or 20 intermediate between the sensor 10 and a target monitor, and/or within an intervening monitor, such as patient monitor 12 or multi-parameter monitor 16, or other electronic device. For example, in one embodiment, the artifact identification of block 62 includes the timing and frequency of artifacts 64. This time and frequency information may be used to locate the corresponding portion of signal components within one or more wavelet decomposition levels (as discussed below) to compensate for the respective artifacts 64.

In addition, the oximetry signals 36 may be processed using a multi-resolution decomposition technique (block 66), such as wavelet decomposition by discrete wavelet transformation using a filter bank. Though wavelet transformation is discussed generally herein, those of ordinary skill in the art will appreciate that other transformation techniques capable of providing the desired time and frequency information may also be employed and are within the scope of the present technique.

As mentioned above with regard to artifact identification, the decomposition of the signal 36 may be accomplished by suitable decomposition algorithms or techniques implemented by one or more processing components 34. These processing components 34 may be disposed within the sensor 10 itself, within the cables 14, 18, or 20 intermediate between the sensor 10 and a target monitor, and/or within an intervening monitor, such as patient monitor 12 or multi-parameter monitor 16, or other electronic device. The one or more processing components 34 that implement signal decomposition may be same as or different than the processing components 34 that implement artifact identification, as discussed above. Furthermore, though FIG. 3 depicts decomposition (block 66) and artifact extraction (62) implemented in parallel, other embodiments are also possible. For example, as will be appreciated by those of ordinary skill in the art, decomposition (block 66) and artifact extraction (block 62) may be implemented sequentially or in series as well.

In a wavelet decomposition implementation, each iteration of decomposition yields a low-passed signal component and a high-passed signal component represented as wavelet coefficients 68. As will be appreciated by those of ordinary skill in the art, the low-passed component generally corresponds to an approximation of the signal undergoing decomposition while the high-passed component generally corresponds to detail components of the signal undergoing decomposition. In one iterative implementation, each iteration, i.e., resolution level, of the decomposition decomposes the previous approximation, i.e., low-passed component, to generate an approximation and detail component representative of the previous approximation. In other words, the low-passed component of the previous resolution level is decomposed to yield high and low-passed components at the current resolution level. Because the low-passed components are iteratively decomposed in such an implementation, each previous resolution level may be reproduced by reintegrating the low and high-passed components (i.e., the approximation and details) of the current resolution level. Similarly, the initial signal may be reproduced by reintegrating the current resolution level of approximation and details along with previous resolution levels of detail.

During or subsequent to wavelet decomposition, some or all of the high and/or low-resolution filtered components generated at some or all of the decomposition resolution levels may be processed (block 70) to compensate for artifact signal, thereby generating modified wavelet coefficients 72. For example, the timing and frequency information for the artifacts 64 identified at block 62 may be used to deduct, remove, or modify the respective wavelet decomposition coefficients, such as during signal reconstruction, to compensate for the artifacts 64. In one embodiment, artifact compensation modifies the low-passed components (i.e., approximations) and/or the high-passed components (i.e., the details) based on the frequency and/or time information associated with the identified artifacts 64 to compensate for portions of the signal attributable to the artifacts 64 in the modified coefficients 72.

For example, in one embodiment, the oximetry signal 36 undergoes a three-stage wavelet decomposition to generate the respective high and low-passed components. In this example, artifact compensation is applied to the two high-passed bands of the three-stage decomposition to generate modified coefficients in these two bands. The artifact compensation process may involve setting applicable coefficients or portions of the signal corresponding to an artifact 64 to zero or otherwise reducing the magnitude of the applicable coefficients or portions of the signal. In this manner, the level of detail in the reconstructed signal may be reduced based on the likely correspondence of the detail level to artifacts or noise instead of to physiological signal.

The modified wavelet coefficients 72 generated by artifact compensation may be reconstructed (block 74), such as by an inverse wavelet transform, to generate a clean or artifact-compensated waveform 76. In such an embodiment, the inverse wavelet transform preserves the original physiological data while allowing artifact compensation, as opposed to techniques using synthesized waveforms (such as triangular synthetic waveforms) where physiological information may be lost. This clean waveform 76, in turn, may be processed to determine (block 78) one or more physiological characteristics of interest, such as respiratory information, blood oxygen saturation, pulse rate, and so forth. In one embodiment, the clean waveform is provided to and processed by a monitor or other electronic device what is not configured to compensate for artifacts itself. Though the preceding discussion generally discusses decomposition using wavelet transformation, other decomposition techniques that generate time-frequency and/or time-scale components may also be used in accordance with the present technique.

Figure 4A:
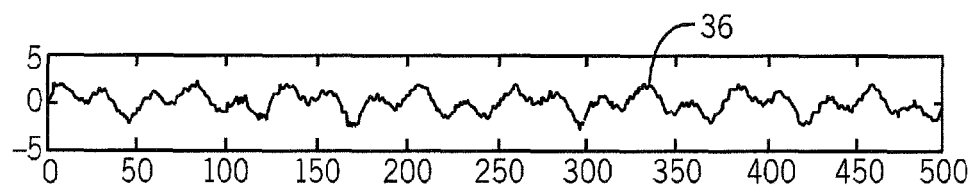
FIG. 4A depicts a waveform representing a pulse oximetry signal to be processed in accordance with aspects of the present technique.
Figure 4B:
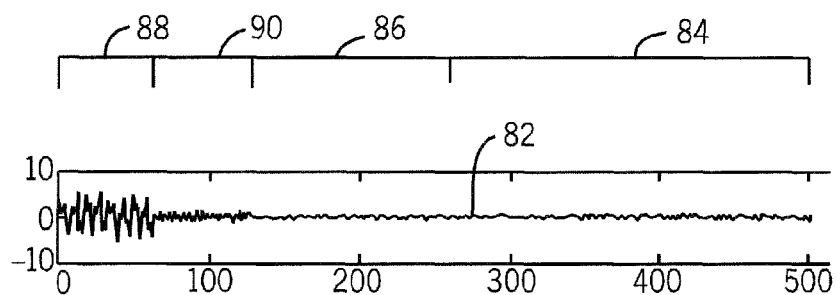
FIG. 4B depicts wavelet transformation of the waveform of FIG. 4A, in accordance with aspects of the present technique.
Figure 4C:
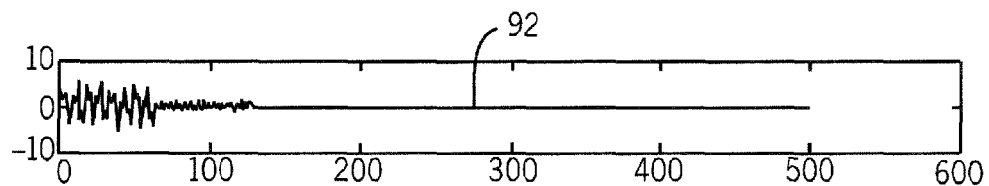
FIG. 4C depicts the wavelet vector of FIG. 4B modified to remove artifact signal, in accordance with aspects of the present technique.
Figure 4D:
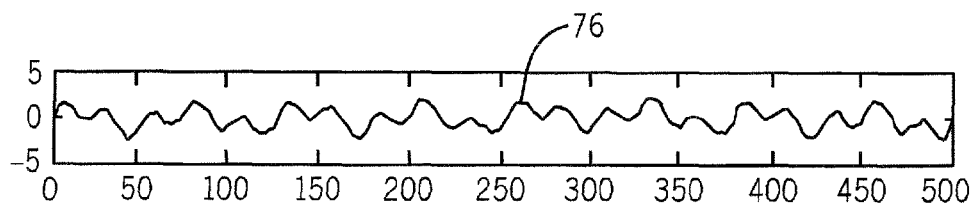
FIG. 4D depicts an output waveform reconstructed from the modified wavelet coefficients of FIG. 4C, in accordance with aspects of the present technique.

Referring now to FIGS. 4A-4D, example waveforms representative of the technique set forth in FIG. 3 are provided for the purpose of illustration. FIG. 4A depicts an oximetry signal 36, as provide in FIG. 3. The signal 36 of FIG. 4A contains artifacts to be compensated. FIG. 4B depicts a three-stage wavelet decomposition 82 of the original signal 36. The three-stage decomposition 82 includes a first high-passed component 84. The first low-passed component was further decomposed to yield a second high-passed component 86 and a second low-passed component that was in turn subsequently decomposed to generate a third low-passed component 88 and a third high-passed component 90. The third low-passed component 88 represents the approximation data for the original signal while the first, second, and third high-passed components 84, 86, 90 represent different levels of detail. FIG. 4C depicts the modified wavelet vector 92 after artifact compensation on the three-stage decomposition 82. In this example, the first and second low-passed bands 84 and 86 correspond to the identified artifact 64 and are set to zero (i.e. removed) in the modified wavelet vector 92, as depicted. The modified wavelet vector 92 provides the wavelet coefficients 72 that may be reconstructed, such as by an inverse wavelet transform, to generate a modified signal 76, such as the depicted output waveform. Artifacts present in the original signal 36 are compensated for in the modified signal 76. The modified signal 76 may be provided to subsequent processes for the determination of physiological characteristics of interest, such as blood oxygen saturation, pulse rate and so forth.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to pulse oximetry, but also to other physiological monitor outputs as well.

What is claimed is:

1. A method for processing a physiological signal, comprising:
   using one or more processors of a sensor, a cable coupling the sensor to a monitor, or an intermediate device disposed between the sensor and the monitor, or any combination thereof, to perform the steps of:
   obtaining a physiological signal in a time domain from the sensor;
   performing a wavelet decomposition on the physiological signal to generate two or more wavelet coefficients;
   identifying one or more artifacts in the physiological signal in the time domain without using the wavelet decomposition results;
   generating an artifact-compensated signal in the time domain based on the one or more artifacts that are identified in the time domain and the two or more wavelet coefficients; and
   providing the artifact-compensated signal to the monitor, wherein the monitor is configured to display the artifact-compensated signal or to display one or more physiological parameters based on the artifact-compensated signal.

2. The method of claim 1, comprising processing the artifact-compensated signal to derive one or more physiological parameters using a processing component of the monitor.

3. The method of claim 2, wherein the monitor is configured to display the one or more physiological parameters, and wherein the physiological signal is an oximetry signal, and the one or more physiological parameters include blood oxygen saturation, pulse rate, tissue water fraction, or tissue or blood carbon dioxide levels, or any combination thereof.

4. The method of claim 1, comprising adjusting the two or more wavelet coefficients to reduce the two or more wavelet coefficients that correspond to the one or more artifacts identified in the time domain, prior to generating the artifact-compensated signal.

5. The method of claim 4, wherein generating the artifact-compensated signal comprises reconstructing the two or more wavelet coefficients using an inverse wavelet transform, after the two or more wavelet coefficients are adjusted to reduce the two or more wavelet coefficients that correspond to the one or more artifacts identified in the time domain.

6. The method of claim 4, wherein adjusting the two or more wavelet coefficients comprises minimizing the two or more wavelet coefficients that correspond to the one or more artifacts identified in the time domain.

7. The method of claim 1, comprising wirelessly transmitting the artifact-compensated signal to the monitor.

8. The method of claim 1, further comprising determining the one or more physiological parameters based on the artifact-compensated signal.

9. A method for processing a physiological signal, comprising:
   using one or more processors of a sensor, a monitor, a cable coupling the sensor to the monitor, or an intermediate device disposed between the sensor and the monitor, or any combination thereof, to perform the steps of:
   obtaining a physiological signal in a time domain from the sensor;
   performing a wavelet decomposition on the physiological signal to generate two or more wavelet coefficients;
   identifying one or more artifacts in the physiological signal in the time domain without using the wavelet decomposition results;
   generating an artifact-compensated signal in the time domain based on the one or more artifacts that are identified in the time domain and the two or more wavelet coefficients; and
   using the artifact-compensated signal to determine one or more physiological parameters.

10. The method of claim 9, wherein the physiological signal is an oximetry signal, and the one or more physiological parameters include blood oxygen saturation, pulse rate, tissue water fraction, or tissue or blood carbon dioxide levels, or any combination thereof.

11. The method of claim 9, comprising adjusting the two or more wavelet coefficients to reduce the two or more wavelet coefficients that correspond to the one or more artifacts identified in the time domain, prior to generating the artifact-compensated signal.

12. The method of claim 11, wherein generating the artifact-compensated signal comprises reconstructing the two or more wavelet coefficients using an inverse wavelet transform, after the two or more wavelet coefficients are adjusted to reduce the two or more wavelet coefficients that correspond to the one or more artifacts identified in the time domain.

13. The method of claim 11, wherein adjusting the two or more wavelet coefficients comprises minimizing the two or more wavelet coefficients that correspond to the one or more artifacts identified in the time domain.

14. The method of claim 11, wherein adjusting the two or more wavelet coefficients comprises setting a value of the two or more wavelet coefficients that correspond to the one or more artifacts to zero.

15. The method of claim 11, wherein the two or more coefficients are adjusted based on time information, frequency information, or a combination thereof, associated with the one or more artifacts identified in the time domain.

16. A method for processing a physiological signal, comprising:
   using one or more processors to perform the steps of:
   applying a wavelet transform to the physiological signal to generate a plurality of coefficients;
   processing the physiological signal in the time domain, without using the wavelet transform results, to identify one or more artifacts within the physiological signal;
   adjusting the plurality of coefficients to reduce one or more coefficients of the plurality of coefficients that correspond to the one or more artifacts identified in the time domain; and
   reconstructing the adjusted plurality of coefficients using an inverse wavelet transform to generate an artifact-compensated signal in the time domain.

17. The method of claim 16, wherein the one or more processors are disposed within a sensor, a monitor, a cable configured to couple the sensor to the monitor, or an intermediate device positioned between the sensor and the monitor, or any combination thereof.

18. The method of claim 16, comprising providing the artifact-compensated signal to an external device that is physically separate from the one or more processors and is configured to display the artifact-compensated signal or to determine one or more physiological parameters based on the artifact-compensated signal.

19. The method of claim 18, comprising processing the artifact-compensated signal to derive one or more physiological parameters of interest using a processing component of the external device.

20. The method of claim 16, wherein the physiological signal is an oximetry signal, and the one or more physiological parameters include blood oxygen saturation, pulse rate, tissue water fraction, tissue or blood carbon dioxide levels, or a combination thereof.

21. The method of claim 16, wherein adjusting the plurality of coefficients comprises removing one or more coefficients that correspond to the one or more artifacts.

* * * * *